(12) United States Patent
Miranda et al.

(10) Patent No.: US 8,455,669 B2
(45) Date of Patent: Jun. 4, 2013

(54) PROCESS FOR EXTRACTING FATTY ACIDS FROM AQUEOUS BIOMASS IN A MEMBRANE CONTACTOR MODULE

(75) Inventors: Andreia Manuela Martins Miranda, Trondheim (NO); Eddy G. Torp, Olso (NO); Inga Marie Aasen, Trondheim (NO); Andrew Guy Livingston, Knebworth (GB)

(73) Assignee: Due Miljo AS, Olso (NO)

( * ) Notice: Subject to any disclaimer, the term of this patent is extended or adjusted under 35 U.S.C. 154(b) by 0 days.

(21) Appl. No.: 13/377,516

(22) PCT Filed: Jun. 10, 2010

(86) PCT No.: PCT/NO2010/000220
§ 371 (c)(1),
(2), (4) Date: Dec. 9, 2011

(87) PCT Pub. No.: WO2010/143974
PCT Pub. Date: Dec. 16, 2010

(65) Prior Publication Data
US 2012/0077255 A1    Mar. 29, 2012

(30) Foreign Application Priority Data
Jun. 10, 2009    (NO) .................................. 20092243

(51) Int. Cl.
*C11B 1/00*    (2006.01)
*C12P 7/64*    (2006.01)

(52) U.S. Cl.
USPC ............................................. 554/8; 435/134

(58) Field of Classification Search
None
See application file for complete search history.

(56) References Cited

U.S. PATENT DOCUMENTS

| 4,275,012 A * | 6/1981 | Kokubo et al. ............... 554/174 |
| 4,579,660 A | 4/1986 | Toushek et al. |
| 2003/0143659 A1 | 7/2003 | Bijl et al. |
| 2005/0170479 A1 | 8/2005 | Weaver et al. |
| 2006/0286205 A1 | 12/2006 | Fichtali et al. |

FOREIGN PATENT DOCUMENTS

| WO | WO 01/60182 A1 | 8/2001 |
| WO | WO 02/076588 A1 | 10/2002 |
| WO | WO 03/092628 A2 | 11/2003 |
| WO | WO 2006/046943 A2 | 5/2006 |

OTHER PUBLICATIONS

Giorno et al., Journal of membrane science, 125:177-187, 1997.*
Rios et al., Journal of membrane science, 242:186-196, 2004.*
Hoq et al., JAOCS, 62(6): 1016-1020, 1985.*
Shahidi et al., Trends in Food Science & Technology, 9:230-240, 1998.*
Li et al., JAOCS, 70(8):745-748, 1993.*
Devos et al., Enzyme and Microbial Technology, 39:548-554, 2006.*

* cited by examiner

*Primary Examiner* — Jennifer Pitrak McDonald
*Assistant Examiner* — Qing Xu
(74) *Attorney, Agent, or Firm* — Knobbe Martens Olson & Bear, LLP (57) ABSTRACT

The present invention relates to a new process for extracting fatty acids from aqueous biomass in a membrane contactor module. The present invention also relates to an integrated process combining biomass concentration and/or diafiltration and fatty acid extraction in said membrane contactor module.

17 Claims, 3 Drawing Sheets

Figure 3: Concentration profile of DHA and C16:0 in the aqueous and organic phases.

PROCESS FOR EXTRACTING FATTY ACIDS FROM AQUEOUS BIOMASS IN A MEMBRANE CONTACTOR MODULE

1. FIELD OF INVENTION

The present invention relates to a new process for extracting fatty acids from aqueous biomass in a membrane contactor module. The present invention also relates to an integrated process combining biomass concentration and/or diafiltration and fatty acid extraction in said membrane contactor module.

2. BACKGROUND OF THE INVENTION

Long-chain omega-3 polyunsaturated fatty acids are essential fatty acids for humans and must be supplied by the diet. Of these, docosahexaenoic acid, C22:6 Δ4,7,10,13,16,19 (DHA) has particular health benefits, and is used not only as a food supplement but also as a pharmaceutical compound for treatment of coronary diseases (Wynn et al, 2005).

DHA is a superior polyenoic acid, as this can easily be converted to other essential polyenoic fatty acids like eicosapentaenoic acid (EPA). Conversion of EPA to DHA is not possible in the human body.

For enrichment of oils to be used in functional foods, and for pharmaceutical applications, there is a need for concentrates of fatty acids or their alkyl ester derivatives. Currently, compositions containing polyunsaturated fatty acids are obtained from fish oils. However, there is a concern that sufficient fish oil will not be available in the future (Lewis et al., 1999). Moreover, reports of the possible accumulation of toxic pollutants, including heavy metals, dioxins and polychlorinated biphenyls (PCBs) from the marine environment into fish lipids, have imposed the needs for extensive purification processes for fish oils intended for human consumption and animal feed (Ratledge, 2004).

An alternative to fish oil is microbial sources. Some marine, heterotrophic microalgae accumulate large quantities of DHA, such as *Crypthecodinium cohnii* (e.g. U.S. Pat. No. 5,407,957) and thraustochytrids (e.g. WO Patent No. 9408467; U.S. Pat. No. 6,509,178). These microorganisms often accumulate more than 50% of their dry weight as lipids, with DHA frequently constituting more than 25% of total lipids (Lewis et al., 1999; Yokochi et al., 1998; Yaguchi et al., 1997). An additional advantage of microbial production of DHA, compared to fish oils, is that DHA is the only, or dominating, long-chain PolyUnsaturated Fatty Acid (PUFA), making the purification process simpler.

Conventionally, marine and vegetable oils are isolated from the biomass by thermal-mechanical processes and/or solvent extraction. When fatty acid alkyl esters are the desired product, the extracted oil is transesterified, often in the presence of a catalyst. In general, the conventional way of obtaining fatty acids from microalgae or fish includes several steps that might be detrimental to the fatty acids, particularly the unstable polyunsaturated fatty acids. The fatty acids are subjected to extensive and tough handling, and high temperature.

Thus, there is a need for new processes for the extraction of fatty acids, particularly LC-PUFA to meet the growing market and the demand for high quality polyunsaturated fatty acids, especially DHA.

3. DESCRIPTION OF THE INVENTION

One object of the invention is to provide a new process for extracting fatty acids.

Another object of the invention is to provide a new process wherein the fatty acids are extracted from aqueous biomass.

Yet another object of the invention is to provide a new process wherein the hydrolysis of the biomass lipids is performed in an aqueous phase.

Yet another object of the invention is to provide a new process for sequencial release of fatty acids with different characteristics.

Yet another object of the invention is to provide a new process for extracting polyunsaturated fatty acids, especially DHA.

These and further objects are achieved by the present invention.

Thus, one aspect of the present invention relates to a process for extracting fatty acids from aqueous biomass in a membrane contactor module M1, comprising the following steps:
a) hydrolysing the lipids of the aqueous biomass to release free fatty acids;
b) feeding the aqueous hydrolyzed biomass containing free fatty acids to the aqueous compartment of said membrane contactor module M1; and
c) extracting the fatty acids across a hydrophobic membrane to the organic compartment of said membrane contactor module M1 containing an organic solvent or solvent mixture.

The new and inventive process represents a simplified process for obtaining fatty acids, particularly DHA or its alkyl ester derivative, from aqueous biomass, without extraction of the oil phase from the biomass. The lipids are hydrolysed in the aqueous biomass. The fatty acids may be converted to their fatty acid ethyl esters in the organic phase by the presence of an alcohol, a catalyst and/or esterification enzyme in the organic phase.

The term aqueous biomass means any biomass suspended, dispersed, homogenized or dissolved in an aqueous medium. The aqueous biomass is preferably a fermentation broth of microorganisms. Oleaginous microorganisms are particularly suitable according to the invention as they contain more than 20% lipids based on the dry weight. The microorganisms may be, but are not limited to, photo or heterotrophic microalgae, preferably thraustochytrids.

However, marine biomass and their by products, especially fish and fish-by products, and also vegetable biomass with a sufficient lipid content, e.g. higher than 10% is encompassed by the present invention. The aqueous biomass may be reconstituted from dried biomass. The aqueous biomass may contain intact cells and disrupted cells.

The water content and the properties of the aqueous biomass should enable proper circulation in the system. The process is particularly applicable to biomass with high water content, e.g. higher than 50%.

The term lipids includes both mono-, di- and triglycerids and phospholipids.

Figure 1:
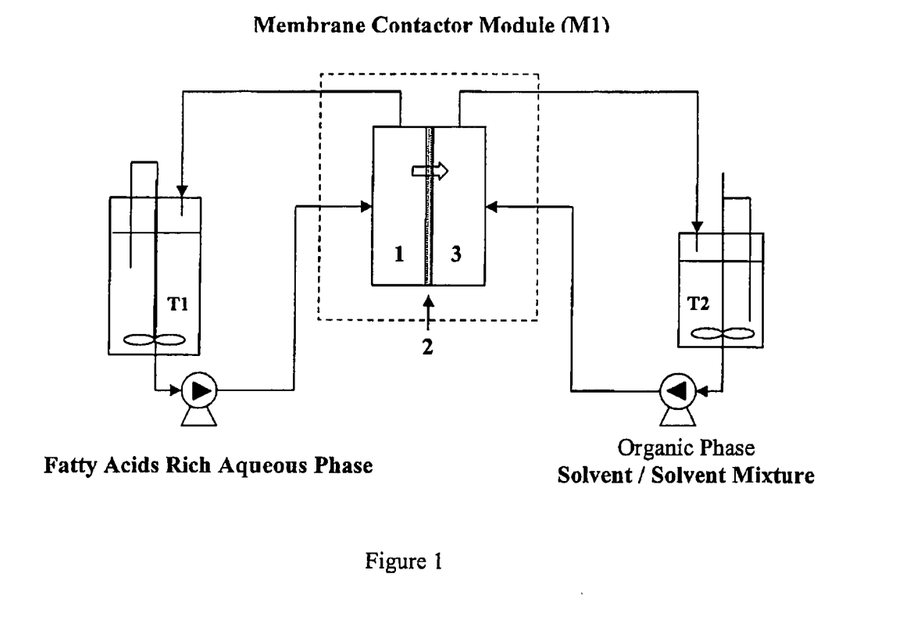
FIG. 1 shows a schematic representation of the process according to the invention. The fatty acid rich aqueous phase is circulated from a biomass tank T1 to the aqueous compartment (1) of the membrane contactor module and back to the biomass tank T1. The solvent/solvent mixture is circulated from a product recovery tank T2 to the organic compartment (3) of the membrane contactor module M1 and back to the product recovery tank T2. The fatty acids are extracted across the hydrophobic membrane (2) by diffusion to the organic compartment where the product of interest accumulates.

A schematic representation of the membrane contactor module is set forth in FIG. 1. The aqueous biomass is circulated from a biomass tank T1 preferably equipped with a stirrer, to the aqueous compartment (1) of the membrane contactor module M1 and back to the biomass tank T1. The organic solvent or solvent mixture is circulated from a product recovery tank T2 to the organic compartment (3) of the membrane contactor module and back to the product recovery tank T2, while the free fatty acids are extracted across the hydrophobic membrane (2) by diffusion to the organic compartment where the product of interest accumulates.

The aqueous biomass rich in fatty acids flows at a higher flow rate than that of the organic phase. Fatty acids are extracted from the aqueous phase into the bulk of the organic phase through the organic solvent wetting the hydrophobic membrane (in FIG. 1, arrow in the membrane module indicates the direction of solute transport). The hydrophobic membrane avoids water breakthrough the membrane and, consequently, the contamination of the organic phase receiving the solute.

The hydrophobic membrane may be made of any hydrophobic polymeric material. Polyimide membranes were preferred, due to their highly hydrophobic characteristics, avoiding water breakthrough the membrane. Different polymers may be used, preferably, but not limited to Lenzing P84 and Matrimid 5218. Membranes may be reinforced by a porous supporting layer made of for instance non-woven polyester baking paper.

Membranes applied in the presented invention may be porous (low ultrafiltration or nanofiltration range) or nonporous membranes. Hydrophobic membrane may also function as a barrier between hydrolysed and unhydrolysed lipids. Membranes may present a rejection greater than 50% for diglycerides molecules containing one or two molecules of DHA, preferably greater than 70%, even more preferably greater than 95%.

Membrane contactor module configuration is adapted in accordance with the membrane design chosen. The membrane utilized in the present invention can be configured with regard to any of the designs known, such as plate and frame, spiral wound, shell and tube, and derived designs thereof. Tubular, hollow fibers or flat sheet membranes may be used.

Lipid hydrolysis is carried out chemically or enzymatically, and is performed directly on the aqueous biomass. Enzymatic hydrolysis may be performed by applying one or more lipases. Mono-, di-, and triglycerides and phospholipids are hydrolysed releasing free fatty acids and the aqueous hydrolyzed biomass is fed to the aqueous compartment of the membrane contactor module. In the membrane contactor the free fatty acids are extracted by concentration gradient diffusion through the hydrophobic membrane to the organic compartment of the membrane contactor module. The organic compartment comprises suitable organic solvent or solvent mixture optionally admixed with alcohols and or catalyst if alkyl ester derivatives of the fatty acids are the preferred product.

The fatty acids to be separated according to the present invention are any fatty acids of interest. It might be medium to long chain fatty acids comprising between fourteen and twenty carbons, either saturated or monounsaturated. Examples are the saturated myristic acid (C14:0), palmitic acid (C16:0), stearic acid (C18:0) and arachidic acid (C20:0), and the monounsaturated oleic acid (C18:1) and gadoleic acid (C20:1). However, preferred fatty acids to be separated according to the present invention are long chain polyunsaturated fatty acids (LC-PUFA) with a carbon chain longer than eighteen carbons and at least three double bonds, particularly EPA and DHA.

According to one embodiment of the invention the fatty acids are released sequencially by enzymatic hydrolysis. In the first stage, saturated and monounsaturated medium to long chain fatty acids are released, especially C16 and C18, by a first lipase. The last stage releases medium to long chain polyunsaturated fatty acids, especially DHA, which can be achieved by leaving the first lipase to act for a longer period of time, or adding a different lipase. In between the first and the last stage, further stages may occur, depending on the fatty acids of interest. The order of the fatty acid release may be changed depending on the experimental conditions. The fatty acids release in the first stage are extracted across the membrane before initiating the next stage.

The lipases used according to the invention may be immobilized on a solid support or dissolved in aqueous biomass.

The enzymes applied are lipases, e.g., but not limited to, lipases of microbial origin, such as 1, 3 position specific and non-specific lipases from *Candida rugosa, Candida cylindracea, Candida antarctica, Pseudomonas* sp, *Mucor javanicus, Mucor mihei, Thermomyces lanuginosus* (Lipozyme TL 100L), and mixtures thereof.

The principle of the hydrolysis process is removal of the undesired fatty acids in the triglyceride molecule, i.e. the saturated and monounsaturated compounds. Attack of the ester bonds between such fatty acids and the glycerol is facilitated by their linear configuration. Saturated and monounsaturated fatty acids are released earlier in the enzymatic reaction and are firstly removed. Consequently, the remaining biomass hydrolysate mixture is enriched in LC-PUFA, particularly DHA. Therefore, either a different enzyme is added to release the LC-PUFA, especially DHA, or the first lipase is left to act for a longer period of time.

More specifically, in a preferred embodiment, palmitic (C16:0), stearic (C18:0) and/or oleic (C18:1) acids, among other easily attacked fatty acids, are removed during first stage of the stepwise enzymatic hydrolysis, preferably more than 50% of their initial composition, more preferably more than 70%, and even more preferably more than 90%. DHA released at this stage should not be greater than 10%, more preferably not greater than 5%. Largest fraction of DHA, among other long chain polyunsaturated fatty acids, is released in the last stage of the stepwise enzymatic hydrolysis either by the action of the first enzyme or a second enzyme.

In a preferred embodiment of the present invention the polyunsaturated fatty acids constitutes at least 50%, preferably 60%, most preferably 80% by weight of the total fatty acids extracted in the last stage of enzymatic hydrolysis.

In an other preferred embodiment DHA constitutes about 60%, preferably about 70%, most preferably about 90% of the total fatty acids extracted in the last stage of enzymatic hydrolysis.

The organic phase circulating from the product recovery tank T2 to the organic compartment of the membrane contactor and back to the product recovery tank is initially filled with a suitable organic solvent or solvent mixture. Preferably, the solvent is a nonpolar solvent, preferably but not limited to hexane, cyclohexane, heptane, pentane, toluene, dichloroethane, dichloromethane, diethylether, ethylacetate, acetone, or any mixtures thereof.

In a preferred embodiment of the present invention, the fatty acids being extracted through the membrane to the organic compartment are converted to their alkyl ester derivative by esterification. Thus, the solvent or solvent mixture circulating from the product recovery tank may further comprise an alcohol selected from the group of lower alkyl alcohols, preferably methanol or ethanol. As such the products of interest accumulating in T2 are ester derivatives of the fatty acids. To facilitate the esterification a catalyst in the form of an acid, a base, an enzyme (lipase) or mixtures thereof may be present in the organic phase circulating from T2 to the organic compartment of the membrane contactor and back to the product recovery tank T2.

To further enhance initial release rates of fatty acids from the aqueous biomass, the biomass might be subjected to pre treatment prior to or simultaneously with the lipid hydrolysis. This pre treatment may include protein and or phospholipid hydrolysis. Any proteases or phospholipases known by those skilled in the art can be used. For instance, proteases from *Streptomyces griseus*, Alcalase, and mixtures thereof, as recommended by the supplier. Phospholipases are preferably of classes A1, A2, and most preferably of classe B.

Salts and other low molecular compounds contaminating the aqueous biomass might be removed by diafiltration. Further, if sub-optimal biomass concentrations are provided, the cell mass should be dewatered. Thus, the present invention relates to a process further comprising a cross-flow filtration module M2 for dewatering of biomass and/or diafiltration.

Thus, another aspect of the present invention relates to an integrated process for extracting fatty acids from aqueous biomass comprising the following steps:

a) dewatering and/or diafiltering said aqueous biomass in a cross-flow filtration module M2, generating a retentate for further processing in a membrane contactor module M1;
b) hydrolysing the lipids in the retentate to release free fatty acids;
c) feeding the hydrolyzed retentate containing free fatty acids to the aqueous compartment of said membrane contactor module M1; and
d) extracting the fatty acids across a hydrophobic membrane to the organic compartment of said membrane contactor module M1 containing an organic solvent or solvent mixture.

Figure 2:
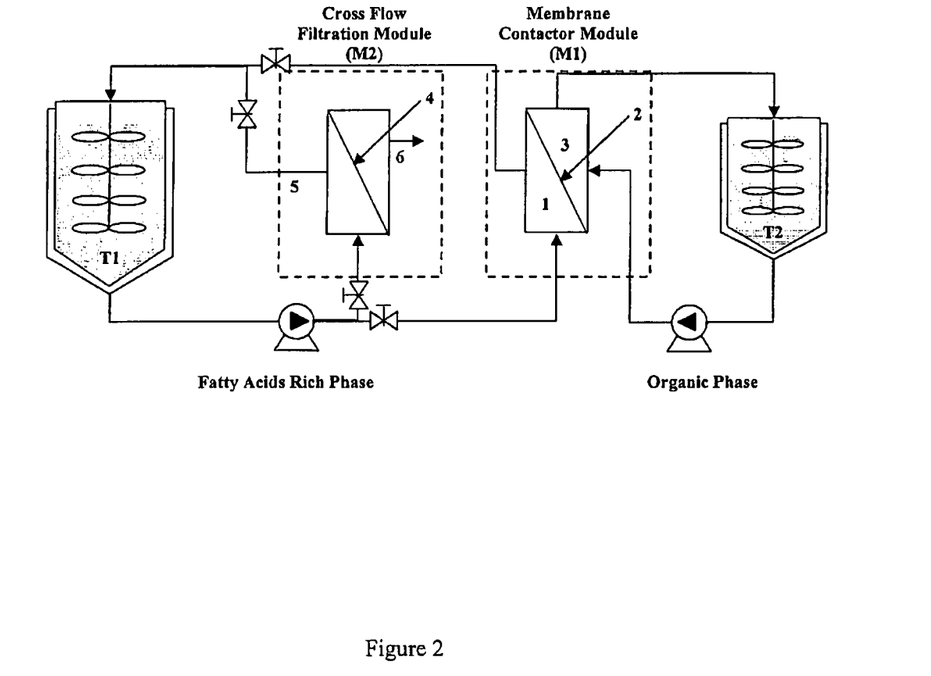
FIG. 2 shows a schematic representation of the integrated process according to the invention. The fatty acid rich aqueous phase is circulated to the cross-flow membrane module M2, and back to the biomass tank T1. Water and low molecular compounds permeates across the membrane (4) generating a waste permeate (6). At a desired cell concentration, the circulation through M2 is stopped, and the aqueous retentate (5) containing the free fatty acids starts circulating into the membrane contactor as explained in FIG. 1.

A schematic representation of the integrated process is set forth in FIG. 2. The fatty acid rich aqueous phase is circulated to the cross-flow membrane module M2, and back to the biomass tank T1. Water and low molecular compounds permeates across the membrane (4) generating a waste permeate (6). At a desired cell concentration, the circulation through M2 is stopped, and the aqueous retentate (5) containing the free fatty acids starts circulating into the membrane contactor as in the first aspect of the present invention.

The cross-flow filtration module M2, generates a concentrated aqueous biomass to be fed into the membrane contactor M1. Concentration of the cell mass from e.g. a fermentation broth by cross-flow filtration, is easily adapted to the succeeding processing in M1 and is preferably set up as an integrated process. Concentration of the cell mass by e.g. centrifugation is not easily adapted to the succeeding processing in M1.

In one embodiment, the aqueous biomass is first circulated from a biomass tank T1 through the cross-flow membrane module M2, whereafter the retentate (5) is circulated to the aqueous compartment (1) of the membrane contactor module M1, extracting the fatty acids to the organic solvent/solvent mixture circulating the organic compartment (3) of the membrane contactor accumulating in a product recovery tank T2.

The permeate generated through the cross-flow membrane contains water and low molecular weight compounds to be discharged.

Step d) above may also comprise a further step of esterification, thus obtaining fatty acid ester derivative.

Both microfiltration (MF) and ultrafiltration (UF) techniques are suitable for the concentration of aqueous biomass. The choice is normally done according to the cell broth characteristics. Ceramic membranes are often preferred to organic membranes in some industrial operations, because of their higher chemical and thermal stability. Cross-flow filtration modules suitable according to the invention contains an inorganic tubular membrane, e.g. membranes made for instance of titanium or zirconium. A suitable inorganic tubular membrane has a cut off in the micro (0.1-10 µm) or ultrafiltration range ($10^3$-$10^6$ Da).

The process according to the invention, is normally operated as a batch process or as a semi-continuous process.

After terminating the process or the integrated process according to the invention, the solvent/solvent mixture might be recovered. Solvent recovery is preferably achieved by organic solvent nanofiltration (OSN) rather than distillation in the proposed system. The organic phase is concentrated while recovering the organic solvent by nanofiltration (existing MET patent). However, any suitable process for solvent mixture recovery might be used.

The free fatty acids or ester derivatives thereof obtained in the product recovery tank T2 is may be further purified by methods well known by persons skilled in the art, such as molecular distillation or chromatography, but particularly by high performance counter current chromatography (HPCCC).

The process according to the invention is a cost effective process for extracting fatty acids or their alkyl ester derivatives. The process also reduces the demand for fish oil. The process is easy to scale up. The fatty acids are of high quality suitable for both food and pharma industry.

5. EXAMPLES

The following examples illustrates the invention.

Example 1

Chemical Versus Enzymatic Hydrolysis of Aqueous Biomass

This example demonstrates that:

With the reaction time and conditions applied, enzymatic hydrolysis of the lipids of the aqueous biomass released about 70% of the amounts fatty acids released by chemical hydrolysis (compare results presented in sub-sections A and B, see values in table 1 and 2).

Pre-treatment of the biomass with protease before enzymatic lipid hydrolysis may be advantageous to facilitate contact between the lipase and the lipids.

A) Chemical Hydrolysis of Aqueous Biomass 1.33 ml water was added to several tubes containing ~200 mg dried biomass in order to give a biomass concentration of 150 g/L dry weight. 5 ml of 0.5M KOH solution in ethanol were added and the solution was blended for 30 seconds (Ultraturrax—UT—9500 rpm). Tubes were incubated at 60° C. in a water bath for 2 hours. 2 ml of water were added after the incubation period and the resulting solution acidified to pH 1. Free fatty acids were extracted washing the hydrolysed solution with three aliquots of 2 ml hexane each. An exact volume of the hexane phase (2 ml), containing the free fatty acids, was withdrawn to a pre-weighed tube and the hexane further evaporated under nitrogen. Free fatty acids were then dissolved in ethanol for analyses.

B) Enzymatic Hydrolysis of Aqueous Biomass

B1) Concentrated Aqueous Biomass (150 g/L DW) without Protease Treatment 300 mg freeze-dried biomass was suspended in 2 ml phosphate buffer (0.1M, pH 7.0 at 37° C.) to reconstitute to a biomass concentration of 150 g/L. 3000 U of lipase LPZ (Lipozyme TL 100L, Novozymes, Denmark) per gram biomass was added after boiling the wet biomass (10 min in a water bath at 98° C.) and cooling to room temperature.

B2) Aqueous Biomass (50 g/L DW) without Protease Treatment 2 ml phosphate buffer (pH 7 at 37° C.) was added to 100 mg of freeze-dried biomass, giving a biomass concentration of 50 g/L dry weight. The cell mass suspension was then boiled for 10 min (at 98° C.) and immediately cooled to room temperature. Two enzyme concentrations were tested for lipase LPZ, namely 1000 and 2000 units per gram biomass.

B3) Aqueous Biomass (50 g/L DW) Pre-Treated by Protease 100 mg of freeze-dried biomass was suspended in 2 ml phosphate buffer (pH 7 at 37° C.), giving a biomass concentration of 50 g/L dry weight. The cell mass suspension was then boiled for 10 min (at 98° C.) and immediately cooled to room temperature. Enzymatic pre-treatment was performed by addition of 20 mg of Alcalase (Novozymes, Denmark) per ml solution. Reaction with the protease lasted for 30 min in a water bath at 60° C. After this period, tube was cooled again to less than 30° C. before addition of lipase. The equivalent to 1000 U of lipase LPZ per gram biomass was added.

All tubes were flushed with nitrogen and properly sealed before being placed on a multi-position stirring plate in an incubator at 37° C., for the desired reaction period. B1 and B3 were incubated for 36 hours and B2 for 12 hours. After incubation, 2 ml of deionised water were added to all tubes. Then, three aliquots of 2 ml hexane were added to the resulting aqueous/hydrolysed solution, mixing between additions.

The resulting emulsion formed by hydrolysed solution and hexane was separated by centrifugation (10 min, 4000 rpm). An exact volume of the hexane phase containing the free fatty acids was withdrawn to a pre-weighed tube and the solvent evaporated under nitrogen. Hydrolysed oil/free fatty acids were then dissolved in ethanol for analysis. Table 1 presents the amounts of main fatty acids released at the different conditions described above.

TABLE 1

Amounts of main fatty acids released per gram of biomass after chemical and enzymatic hydrolysis of aqueous biomass. Analysis by LC-MS

| Fatty Acid | Chemical Hydrolysis | Enzymatic Hydrolysis (using LPZ) | | |
|---|---|---|---|---|
| | | | | |
| (FA) | RV | B1 | B2-2000U | B2-1000U | B3 |
| C16:0 | 153 | 124 | 124 | 111 | 98 |
| C18:1 | 85 | 65 | 68 | 62 | 50 |
| C22:6 | 137 | 81 | 75 | 60 | 29 |

Rf—Reference Values

Comparison of B2 and B3 shows that protease pre-treatment had no effect on the final yield of released fatty acids, however (data not shown), facilitates contact between the lipase and the lipids and increases the initial rates, thereby reducing the total reaction time. Results from enzymatic hydrolysis was comparable with chemical hydrolysis, especially for the concentrated aqueous biomass (B1). 70% of total fatty acids were recovered, namely 81% of palmitic acid (C16:0), 77% of oleic acid (C18:1) and 46% of DHA (C22:6).

Example 2

Sequential Release of Fatty Acids by Enzymatic Hydrolysis

This example demonstrates the hydrolysis efficiency of four commercially available microbial lipases: *Candida rugosa* (CR), *Mucor javanicus* (MJ), *Pseudomonas* sp (PS), all from Sigma Aldrich (Germany), and Lipozyme (LPZ) from Novozymes (Denmark).

200 mg freeze-dried biomass was suspended in 4 ml phosphate buffer (0.1M, pH 7 for CR, PS and LPZ, and pH8 for MJ, at 37° C.) to a biomass concentration of 50 g/L dry weight. Tubes were placed in a water bath at 98° C. and boiled for 10 minutes. After this period, tubes were immediately removed from the water bath and cooled to room temperature. Enzyme amounts equivalent to 2000 U per gram biomass were added to the tubes. After flushing with nitrogen and properly sealed, tubes were placed on a multi-stirring plate (350 rpm) in an incubator at 37° C. After 24 hours incubation, 4 ml deonised water were added to each tube. Then, five aliquots of 2 ml hexane were added to the resulting aqueous/hydrolysed solution, mixing between additions. The resulting emulsion formed by hydrolysed solution and hexane was separated by centrifugation (10 min, 4000 rpm). An exact volume of the hexane phase containing the free fatty acids was withdrawn to a pre-weighed tube and the solvent evaporated under nitrogen. Hexane was then evaporated under nitrogen and the free fatty acids dissolved in ethanol for analysis. Table 2 shows the total amount of the main fatty acids released in each case.

TABLE 2

Amount of main fatty acids released by enzymatic hydrolysis of aqueous biomass (24 hours reaction) for the four enzymes in study (*Candida rugosa*—CR, Lipozyme—LPZ, *Mucor javanicus*—MJ and *Pseudomonas* sp—PS) and an enzyme concentration of 2000U per gram biomass. Analysis by LC-MS

| Fatty Acid | Concentration (mg FA/g biomass) | | | | |
|---|---|---|---|---|---|
| (FA) | RV | CR | LPZ | PS | MJ |
| C16:0 | 153 | 115 | 131 | 149 | 155 |
| C18:1 | 85 | 60 | 57 | 74 | 70 |
| C22:6 | 137 | 23 | 45 | 95 | 26 |

RV—Reference Values

The results show that LPZ released the highest amounts of fatty acids during the reaction period. However, CR and MJ were more selective, i.e. they removed preferentially C16:0 and C18:1, with a complete recovery of C16:0 while using MJ. Therefore, MJ may be used in the first stage of the desired stepwise hydrolysis of the present invention, and PS in a second stage. In a possible scenario, access of lipase PS to ester bond between DHA (C22:6) and the glyceride molecule will be facilitated after removal of C16:0 and C18:1 by lipase MJ.

Example 3

Fatty Acids Separation Using a Membrane Contactor

The experiments described below were carried out to demonstrate the efficiency of the membrane contactor and polyimide membranes for the fatty acids extraction without direct contact of the organic solvent with the aqueous solution. From these preliminary experiments it was surprisingly found that the hydrophobic polyimide membranes function perfectly as a barrier between aqueous (fatty acids rich phase) and organic (extraction solvent) phases. Water breakthrough was not observed and fatty acids were successful extracted from the aqueous to the organic phase.

For preliminary tests for the study of mass transfer in the membrane contactor, the solution rich in fatty acids was prepared by direct chemical hydrolysis of microalgae biomass. 10 g of freeze-dried biomass were suspended in 300 ml 0.5M KOH in ethanol, homogenized (9500 rpm, Ultraturrax) and left overnight with continuous stirring at room temperature. Then, the flask was incubated in a water bath at 60° C. for 30 minutes. After cooling to room temperature, 150 ml deonised water were added. Aqueous solution containing the salts of fatty acids was then acidified to pH 1 using a solution of 6M HCl, in order to obtain the free fatty acids.

Hydrophobic membrane used was a polyimide membrane. Matrimid 5218 was chosen because of the well known hydrophobic characteristics of this polymer. Flat sheet matrimid membrane, prepared in N-methylpyrrolidinone (NMP), had a filtration area of 41 $cm^2$, a molecular weight cut off (MWCO) ~5 kDa.

As described previously, the two liquid circuits, separated by the hydrophobic membrane, namely the fatty acids rich phase and the organic phase, were in continuous circulation (gear pump), one on each side of the membrane contactor. Fatty acids rich phase was circulating at a higher flow rate (90 L/h) than that of the organic phase (20 L/h), in order to avoid the water breakthrough and also to facilitate the membrane to be wetted by the solvent. Initial volumes of fatty acids rich phase and organic phase were 500 ml and 100 ml, respectively. Experiments were conducted at room temperature and atmospheric pressure. Due to some limitations of the experimental set-up capacity, trials were run for a maximum of 22 hours. Samples were collected periodically until 22 hours running. Collected samples were methylated and analysed by GC.

TABLE 3

Initial and final composition of main fatty acids in the aqueous and organic phases circulating in the membrane contactor.

| | Total amount (initial; final-mg) | |
|---|---|---|
| Fatty Acid | Fatty Acids Rich Phase | Organic Phase |
| C16:0 | 710; 480 | 0; 230 |
| C18:1 | 604; 426 | 0; 178 |
| C22:6 | 814; 554 | 0; 260 |

Extraction yields reached at this stage were about 30-32%, i.e. about 30-32% of main fatty acids in the microalgae biomass were recovered from the emulsion formed after chemical hydrolysis.

Overall mass transfer coefficient, OMTC—$K_{aq}$, was calculated based on the variation of DHA (C22:6) concentration in the organic phase during the 22 hours running. The estimated value for $K_{aq}$ was $7.0 \times 10^{-7}$ $m.s^{-1}$.

Example 4

Fatty Acids Separation Using a Membrane Contactor

The experiment described in the present example was run in the same basis as Example 3. However, the initial volumes of both phases were changed and a new membrane was used in order to improve the separation performance.

5 g of freeze-dried biomass were suspended in 150 ml 0.5M KOH in ethanol, homogenized (9500 rpm, Ultraturrax) and left overnight with continuous stirring at room temperature. Then, the flask was incubated in a water bath at 60° C. for 30 minutes. After cooling to room temperature, 75 ml deonised water were added. Aqueous solution containing the salts of fatty acids was then acidified to pH 1 using a solution of 6M HCl, in order to obtain the free fatty acids.

Hydrophobic membrane used was again a flat sheet polyimide membrane, with a filtration area of 41 $cm^2$, prepared with Matrimid 5218 and N,N-Dimethylformamide (DMF), and with a molecular weight cut off (MWCO) of ~35 kDa.

Experimental set up and flow rates were the same as in Example 3. Initial volumes of fatty acids rich phase and organic phase were 250 ml and 200 ml, respectively. Organic phase contained 0.1% BHT (Butylated hydroxytoluene) in order to prevent oxidation. Experiments were conducted at room temperature and atmospheric pressure. Collected samples were methylated and analysed by GC. Initial and final concentrations of main fatty acids in the feed (fatty acids rich phase) and product phase (organic phase) are shown in table 4.

TABLE 4

Initial and final composition of main fatty acids in the aqueous and organic phases circulating in the membrane contactor.

| Fatty Acid | Total amount (initial; final-mg) | |
|---|---|---|
| | Fatty Acids Rich Phase | Organic Phase |
| C16:0 | 625; 21 | 0; 599 |
| C18:1 | 315; 4 | 0; 310 |
| C22:6 | 875; 36 | 0; 838 |

Separation performance was considerably improved if compared with results presented in Example 3. Extraction yields reached were between 95-98%, i.e. about 95-98% of main fatty acids in the microalgae biomass were recovered from the emulsion formed after chemical hydrolysis.

Overall mass transfer coefficient, OMTC—$K_{aq}$, was calculated based on the variation of DHA (C22:6) concentration in the organic phase. The estimated value for $K_{aq}$ was $17.0 \times 10^{-7}$ m.s$^{-1}$.

Example 5

Fractionation of Fatty Acids by Simultaneous Enzymatic Hydrolysis and Separation from the Aqueous Biomass in a Membrane Contactor The experiments described below were conducted in order to prove that fractionation between saturated and polyunsaturated fatty acids may be achieved by performing simultaneous hydrolysis and separation of fatty acids from aqueous biomass to an organic phase in a membrane contactor system at mild conditions.

The solution rich in fatty acids was prepared by enzymatic hydrolysis of microalgae biomass. 5 g of freeze-dried biomass were suspended in 100 ml of 0.1M potassium phosphate buffer (pH 5), and heated to 98° C. in a water bath for 10 minutes. For pretreatment, 1 g of phospholipase was added to the biomass suspension which was further placed in a water bath at 50° C. for 2 hours with continuous stirring. After finishing the pre-treatment, the biomass suspension was cooled to around 30° C. pH was then adjusted to 7, 100 ml of ethanol were added to the biomass suspension, and the flask was incubated in a water bath at 37° C. First lipase was added when the optimum temperature was reached. Recirculation of the biomass suspension to the aqueous compartment of the membrane contactor was initiated 2 hours after the beginning of the triglycerides hydrolysis. The second lipase was added to the biomass suspension when saturated fatty acids were satisfactorily removed and solvent in the organic phase was replaced by clean solvent.

Hydrophobic membrane used and the experimental set up was the same as in example 4, as well as the operating conditions, e.g. flow rates. Initial volumes of fatty acids rich phase and organic phase were 250 ml and 200 ml, respectively. Solvent circulating in the organic compartment contained 0.1% BHT (Butylated hydroxytoluene) in order to prevent oxidation. Experiments were conducted at atmospheric pressure. Samples were collected periodically and immediately methylated to be further analysed by GC.

Figure 3:
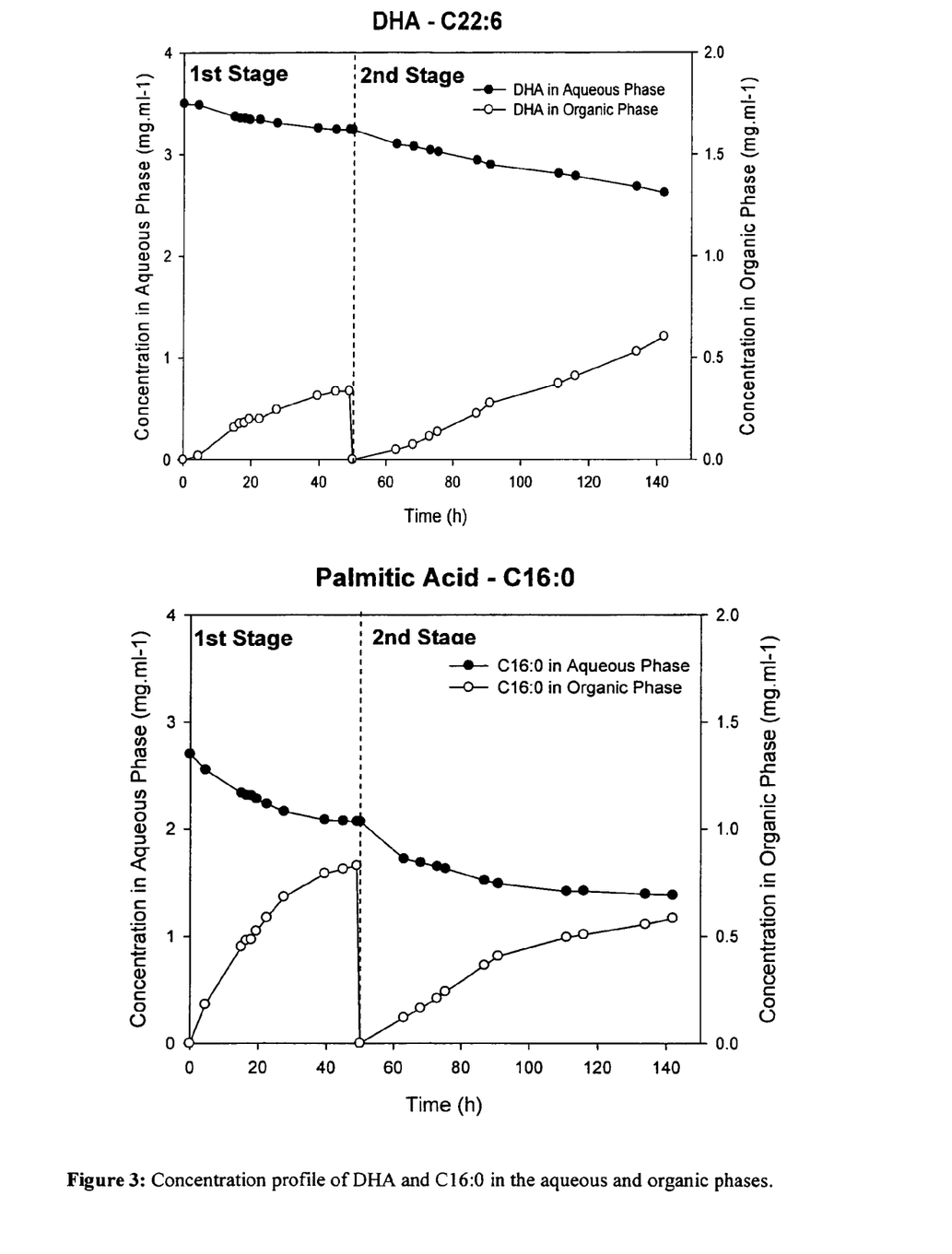
FIG. 3 shows concentrations of DHA and palmitic acid in the aqueous and organic phases throughout the experiment. Plots are divided in two sections. $1^{st}$ stage corresponds to the separation achieved when the first lipase was in use. As expected, concentration of C16:0 in the organic phase was greater than the concentration of DHA at the end of this stage. $2^{nd}$ stage started when second lipase was added for the hydrolysis of remaining glycerides, consequently more DHA was released and concentration of DHA in the organic phase increased linearly.

As depicted in FIG. 3, from these experiments it was proved that saturated fatty acids, namely C16:0, were preferably extracted in the first stage, while polyunsaturated fatty acids remain in the aqueous phase. By the addition of the second lipase, remaining glycerides were hydrolysed. Therefore, at the second stage of the experiment, an enhancement of the mass transfer rates of polyunsaturated fatty acids, namely DHA, was observed. By the end of this experiment, DHA transport was still increasing linearly, whilst C16:0 was stabilizing. Overall mass transfer coefficient obtained for DHA was $0.36 \times 10^{-7}$ m.s$^{-1}$ and for C16:0 was $1.48 \times 10^{-7}$ m.s$^{-1}$, in the first stage.

Example 6

Cell Harvesting/Diafiltration Using Cross Flow Microfiltration—CFMF

Fermentation broth was concentrated from 45-50 g/L to 180 g/L by cross flow microfiltration.

CFMF system and tubular membranes used in the present tests were supplied by Orelis (Novasep, Applexion, France). Microfiltration Kerasep™ ceramic membranes utilized, namely KERMBMM1 and KERMBMM2, had a cut-off of 100 nm and 200 nm, respectively, and a filtration area of 0.008 m$^2$ (as given by the supplier).

Fresh fermentation broth with an initial cell concentration of about 45-50 g/L (dry weight basis) was continuously recycled from and to the vessel T1 through the tubular membrane in the membrane filtration module (M2) by a mono-screw pump, with a constant speed of 5 m/s (as indicated by the supplier). Filtration flux was calculated based on the permeate weight and the concentration factor based on the difference between the dry weight of the original fermentation broth and the retentate solution at the end of the experiment.

Different transmembrane pressures (TMP) were compared using the membrane KERMBMM1. Filtration flux obtained after 30 minutes operation at each TMP is presented in table 5.

TABLE 5

Permeate flux for the same microfiltration membrane (KERMBMM1) operating at different transmembrane pressures ($P_{in}$-$P_{out}$ (bar); initial broth concentration ~45 g/L; T = 25° C., v = 5 m/s; pH ~7).

| TMP (bar, $P_{in}$-$P_{out}$) | Flux (L/m$^2$/h/bar) |
|---|---|
| 0.6 (0.7-0.5) | 164 |
| 0.7 (0.8-0.6) | 184 |
| 1.1 (1.2-1.0) | 102 |
| 1.3 (1.4-1.2) | 82 |

A TMP of 0.7 bar ($P_{in}$=0.8 bar; $P_{out}$=0.6 bar) was found as the ideal for this system. Performances of two membranes in study were evaluated according to the permeation flux and final cell concentration achieved while working at same TMP (table 6).

TABLE 6

Flux variation with cell concentration for two microfiltration membranes (KERMBMM1-100 nm and KERMBMM2-200 nm), operating at same transmembrane pressure ($P_{in} = 0,8$ bar-$P_{out} = 0.6$ bar; initial broth concentration ~45 g/L; T = 25° C., v = 5 m/s; pH ~7).

| Cell Concentration (g/L) | Flux (L/m²/h/bar) | |
| --- | --- | --- |
| | KERMBMM1 | KERMBMM2 |
| 100 | 130 | 302 |
| 130 | 74 | 280 |
| 180 | — | 186 |

It was evident that for the same broth concentration and operating conditions, membrane KERMBMM2 (200 nm) had the best performance. A final cell concentration of 180 g/L was reached.

The invention claimed is:

1. A process for extracting free fatty acids from aqueous biomass in a membrane contactor module, comprising the following steps:
   a) hydrolyzing lipids of the aqueous biomass to release free fatty acids;
   b) feeding the aqueous hydrolyzed biomass containing free fatty acids to an aqueous compartment of said membrane contactor module; and
   c) extracting the free fatty acids across a hydrophobic membrane to an organic compartment of said membrane contactor module containing an organic solvent or solvent mixture.

2. The process according to claim 1, wherein the aqueous biomass is circulated from a biomass tank to the aqueous compartment of the membrane contactor module and back to the biomass tank, and wherein the organic solvent or solvent mixture is circulated from a product recovery tank to the organic compartment of the membrane contactor module and back to the product recovery tank, while the free fatty acids are extracted across the hydrophobic membrane.

3. The process according to claim 1, wherein the lipid hydrolysis is enzymatic and comprises applying one or more lipases.

4. The process according to claim 1, wherein the fatty acids are released sequentially, wherein saturated and monounsaturated medium to long chain fatty acid are released in a first stage and polyunsaturated fatty acids are released in a second stage.

5. The process according to claim 4, wherein the fatty acid released in the first stage are extracted across the membrane before initiating a next stage.

6. The process according to claim 4, wherein the fatty acids of the first stage are obtained by hydrolysis with a first lipase, and the fatty acids of the second stage are obtained by allowing the first lipase to act for a longer period of time or by adding a second lipase.

7. The process according to claim 1, further comprising a step of esterification of the fatty acids to their alkyl ester derivative in the organic compartment.

8. The process according to claim 1, wherein the aqueous biomass is subjected to protease treatment before lipid hydrolysis.

9. The process according to claim 1, wherein the aqueous biomass is subjected to phospholipase treatment before lipid hydrolysis.

10. The process according to claim 1, wherein said organic solvent is a nonpolar solvent.

11. The process according to claim 7, wherein said organic solvent or solvent mixture comprises a lower alkyl alcohol.

12. The process according to claim 1, wherein said organic solvent or solvent mixture comprises a catalyst in the form of an acid, a base, an enzyme or a mixture thereof.

13. The process according to claim 1, wherein the aqueous biomass is subjected to dewatering and/or diafiltering treatment.

14. An integrated process for extracting fatty acids from aqueous biomass comprising the following steps:
   a) dewatering and/or diafiltering said aqueous biomass in a cross-flow filtration module, thus generating a retentate for further processing in a membrane contactor module;
   b) hydrolyzing lipids in the retentate to release free fatty acids;
   c) feeding the hydrolyzed retentate containing free fatty acids to an aqueous compartment of said membrane contactor module; and
   d) extracting the fatty acids across a hydrophobic membrane to an organic compartment of said membrane contactor module containing an organic solvent or solvent mixture.

15. The process according to claim 14, wherein, in said step of dewatering and/or diafiltering, the aqueous biomass is first circulated from a biomass tank through the cross-flow filtration module, wherein water and low molecular compounds permeate across the membrane generating a waste permeate, whereafter the retentate is circulated to the aqueous compartment of the membrane contactor module, and fatty acids are extracted to an organic solvent or solvent mixture circulating the organic compartment of the membrane contactor, and the extracted fatty acids are accumulated in a product recovery tank.

16. The process according to claim 10, wherein said nonpolar solvent is selected from the group consisting of hexane, cyclohexane, heptane, pentane, toluene, dichloroethane, dichloromethane, diethylether, ethylacetate, acetone.

17. The process according to claim 11, wherein said lower alkyl alcohol is selected from the group consisting of methanol and ethanol.

* * * * *